United States Patent

Arora et al.

(10) Patent No.: US 9,516,758 B2
(45) Date of Patent: Dec. 6, 2016

(54) EXTREMELY STRETCHABLE ELECTRONICS

(71) Applicant: MC10, Inc., Cambridge, MA (US)

(72) Inventors: William J. Arora, Bellevue, WA (US); Roozbeh Ghaffari, Cambridge, MA (US)

(73) Assignee: MC10, Inc., Cambridge, MA (US)

(*) Notice: Subject to any disclaimer, the term of this patent is extended or adjusted under 35 U.S.C. 154(b) by 0 days.

(21) Appl. No.: 14/488,544

(22) Filed: Sep. 17, 2014

(65) Prior Publication Data

US 2015/0069617 A1    Mar. 12, 2015

Related U.S. Application Data

(63) Continuation of application No. 13/767,262, filed on Feb. 14, 2013, now Pat. No. 9,012,784, which is a (Continued)

(51) Int. Cl.
*H05K 1/18* (2006.01)
*H05K 3/32* (2006.01)
(Continued)

(52) U.S. Cl.
CPC ........... *H05K 1/189* (2013.01); *H01L 23/4985* (2013.01); *H01L 23/52* (2013.01);
(Continued)

(58) Field of Classification Search
CPC ............................... H05K 1/189; H05K 3/326
See application file for complete search history.

(56) References Cited

U.S. PATENT DOCUMENTS 3,716,861 A    2/1973    Root
3,805,427 A    4/1974    Epstein
(Continued)

FOREIGN PATENT DOCUMENTS

EP    0585670 A2    3/1994
JP    05-087511 A    4/1993
(Continued)

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
(Continued)

*Primary Examiner* — Jeremy C Norris
(74) *Attorney, Agent, or Firm* — Nixon Peabody LLP

(57) ABSTRACT

In embodiments, the present invention may attach at least two isolated electronic components to an elastomeric substrate, and arrange an electrical interconnection between the components in a boustrophedonic pattern interconnecting the two isolated electronic components with the electrical interconnection. The elastomeric substrate may then be stretched such that the components separate relative to one another, where the electrical interconnection maintains substantially identical electrical performance characteristics during stretching, and where the stretching may extend the separation distance between the electrical components to many times that of the un-stretched distance.

33 Claims, 8 Drawing Sheets

Related U.S. Application Data continuation of application No. 12/616,922, filed on Nov. 12, 2009, now Pat. No. 8,389,862, which is a continuation-in-part of application No. 12/575,008, filed on Oct. 7, 2009.

(60) Provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.
    *H01L 23/498*     (2006.01)
    *H01L 23/52*     (2006.01)
    *H01L 23/528*     (2006.01)
    *H01L 23/00*     (2006.01)
    *H05K 1/02*     (2006.01)
    *A61F 2/958*     (2013.01)

(52) U.S. Cl.
    CPC .......... *H01L 23/528* (2013.01); *H01L 23/564* (2013.01); *H05K 1/0283* (2013.01); *H05K 3/326* (2013.01); *A61F 2/958* (2013.01); *H01L 2924/0002* (2013.01); *Y10T 29/4913* (2015.01); *Y10T 29/49155* (2015.01); *Y10T 29/49204* (2015.01)

(56) References Cited

U.S. PATENT DOCUMENTS

| | | |
|---|---|---|
| 3,949,410 A | 4/1976 | Bassous |
| 4,058,418 A | 11/1977 | Lindmayer |
| 4,304,235 A | 12/1981 | Kaufman |
| 4,392,451 A | 7/1983 | Mickelsen et al. |
| 4,416,288 A | 11/1983 | Freeman |
| 4,471,003 A | 9/1984 | Cann |
| 4,487,162 A | 12/1984 | Cann |
| 4,658,153 A | 4/1987 | Brosh |
| 4,663,828 A | 5/1987 | Hanak |
| 4,761,335 A | 8/1988 | Aurichio et al. |
| 4,763,275 A | 8/1988 | Carlin |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,147,519 A | 9/1992 | Legge |
| 5,178,957 A | 1/1993 | Kolpe et al. |
| 5,204,144 A | 4/1993 | Cann et al. |
| 5,306,917 A | 4/1994 | Black |
| 5,313,094 A | 5/1994 | Beyer et al. |
| 5,331,966 A | 7/1994 | Bennett et al. |
| 5,360,987 A | 11/1994 | Shibib |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | DeLonzor et al. |
| 5,501,893 A | 3/1996 | Laermer et al. |
| 5,525,815 A | 6/1996 | Einset |
| 5,539,935 A | 7/1996 | Rush, III |
| 5,545,291 A | 8/1996 | Smith et al. |
| 5,549,108 A | 8/1996 | Edwards et al. |
| 5,560,974 A | 10/1996 | Langley |
| 5,567,975 A | 10/1996 | Walsh |
| 5,625,471 A | 4/1997 | Smith |
| 5,648,148 A | 7/1997 | Simpson |
| 5,687,737 A | 11/1997 | Branham et al. |
| 5,691,245 A | 11/1997 | Bakhit et al. |
| 5,746,207 A | 5/1998 | McLaughlin |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,811,790 A | 9/1998 | Endo |
| 5,817,008 A | 10/1998 | Rafert et al. |
| 5,817,242 A | 10/1998 | Biebuyck et al. |
| 5,824,186 A | 10/1998 | Smith et al. |
| 5,860,974 A | 1/1999 | Abele |
| 5,871,443 A | 2/1999 | Edwards et al. |
| 5,904,545 A | 5/1999 | Smith et al. |
| 5,907,189 A | 5/1999 | Mertol |
| 5,907,477 A | 5/1999 | Tuttle et al. |
| 5,915,180 A | 6/1999 | Hara et al. |
| 5,917,534 A | 6/1999 | Rajeswaran |
| 5,919,155 A | 7/1999 | Lattin et al. |
| 5,928,001 A | 7/1999 | Gillette et al. |
| 5,955,781 A | 9/1999 | Joshi et al. |
| 5,976,683 A | 11/1999 | Liehrr et al. |
| 5,978,972 A | 11/1999 | Stewart |
| 5,998,291 A | 12/1999 | Bakhit et al. |
| 6,024,702 A | 2/2000 | Iversen |
| 6,057,212 A | 5/2000 | Chan et al. |
| 6,063,046 A | 5/2000 | Allum |
| 6,080,608 A | 6/2000 | Nowak |
| 6,097,984 A | 8/2000 | Douglas |
| 6,121,110 A | 9/2000 | Hong |
| 6,165,391 A | 12/2000 | Vedamuttu |
| 6,165,885 A | 12/2000 | Gaynes et al. |
| 6,171,730 B1 | 1/2001 | Kuroda et al. |
| 6,181,551 B1 | 1/2001 | Herman et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,301,500 B1 | 10/2001 | Van Herk |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Willson et al. |
| 6,344,616 B1 | 2/2002 | Yokokawa |
| 6,360,615 B1 | 3/2002 | Smela |
| 6,380,729 B1 | 4/2002 | Smith |
| 6,403,397 B1 | 6/2002 | Katz |
| 6,413,790 B1 | 7/2002 | Duthaler et al. |
| 6,414,783 B2 | 7/2002 | Zavracky et al. |
| 6,417,025 B1 | 7/2002 | Gengel |
| 6,420,266 B1 | 7/2002 | Smith et al. |
| 6,421,016 B1 | 7/2002 | Phillips |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,504,105 B1 | 1/2003 | Acocella et al. |
| 6,517,995 B1 | 2/2003 | Jacobson et al. |
| 6,527,964 B1 | 3/2003 | Smith et al. |
| 6,555,408 B1 | 4/2003 | Jacobsen et al. |
| 6,566,744 B2 | 5/2003 | Gengel |
| 6,567,158 B1 | 5/2003 | Falcial |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,613,979 B1 | 9/2003 | Miller et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |

(56) References Cited

U.S. PATENT DOCUMENTS

| | | |
|---|---|---|
| 6,666,821 B2 | 12/2003 | Keimel |
| 6,667,548 B2 | 12/2003 | O'Connor et al. |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,762,510 B2 | 7/2004 | Fock et al. |
| 6,775,906 B1 | 8/2004 | Silverbrook |
| 6,780,696 B1 | 8/2004 | Schatz |
| 6,784,450 B2 | 8/2004 | Pan et al. |
| 6,784,844 B1 | 8/2004 | Boakes et al. |
| 6,787,052 B1 | 9/2004 | Vaganov |
| 6,814,898 B1 | 11/2004 | Deeman et al. |
| 6,816,380 B2 | 11/2004 | Credelle et al. |
| 6,826,509 B2 | 11/2004 | Crisco, III et al. |
| 6,836,744 B1 | 12/2004 | Asphahani et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,885,030 B2 | 4/2005 | Onozuka et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whitford et al. |
| 6,950,220 B2 | 9/2005 | Abramson et al. |
| 6,965,160 B2 | 11/2005 | Cobbley |
| 6,967,362 B2 | 11/2005 | Nam et al. |
| 6,984,934 B2 | 1/2006 | Moller et al. |
| 6,987,314 B1 | 1/2006 | Yoshida |
| 6,989,285 B2 | 1/2006 | Ball |
| 7,029,951 B2 | 4/2006 | Chen et al. |
| 7,033,961 B1 | 4/2006 | Smart et al. |
| 7,054,784 B2 | 5/2006 | Flentov et al. |
| 7,067,903 B2 | 6/2006 | Tachibana et al. |
| 7,081,642 B2 | 7/2006 | Onozuka et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Weiser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,223,632 B2 | 5/2007 | Onozuka et al. |
| 7,252,664 B2 | 8/2007 | Nasab et al. |
| 7,253,442 B2 | 8/2007 | Huang et al. |
| 7,255,919 B2 | 8/2007 | Sakata et al. |
| 7,265,298 B2 | 9/2007 | Maghribi et al. |
| 7,291,146 B2 | 11/2007 | Steinke et al. |
| 7,291,540 B2 | 11/2007 | Mech et al. |
| 7,293,353 B2 | 11/2007 | Matsuda |
| 7,302,751 B2 | 12/2007 | Hamburgen |
| 7,337,012 B2 | 2/2008 | Maghribi et al. |
| 7,374,968 B2 | 5/2008 | Kornilovich et al. |
| 7,425,523 B2 | 9/2008 | Ikemizu et al. |
| 7,487,587 B2 | 2/2009 | Vanfleteren et al. |
| 7,491,892 B2 | 2/2009 | Wagner et al. |
| 7,509,835 B2 | 3/2009 | Beck |
| 7,521,292 B2 | 4/2009 | Rogers et al. |
| 7,526,389 B2 | 4/2009 | Greenwald et al. |
| 7,557,367 B2 | 7/2009 | Rogers et al. |
| 7,593,086 B2 | 9/2009 | Jeong et al. |
| 7,618,260 B2 | 11/2009 | Daniel et al. |
| 7,622,367 B1 | 11/2009 | Nuzzo et al. |
| 7,629,691 B2 | 12/2009 | Roush et al. |
| 7,633,761 B2 | 12/2009 | Kim |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,199 B2 | 6/2010 | Fernandes et al. |
| 7,727,575 B2 | 6/2010 | Kaplan et al. |
| 7,742,795 B2 | 6/2010 | Stone et al. |
| 7,759,167 B2 | 7/2010 | Vanfleteren et al. |
| 7,799,699 B2 | 9/2010 | Nuzzo et al. |
| 7,842,780 B2 | 11/2010 | Kaplan et al. |
| 7,857,781 B2 | 12/2010 | Noda et al. |
| 7,871,661 B2 | 1/2011 | Maghribi et al. |
| 7,884,540 B2 | 2/2011 | Sung et al. |
| 7,932,123 B2 | 4/2011 | Rogers et al. |
| 7,935,056 B2 | 5/2011 | Zdeblick |
| 7,943,491 B2 | 5/2011 | Nuzzo et al. |
| 7,960,246 B2 | 6/2011 | Flamand et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,107,248 B2 | 1/2012 | Shin et al. |
| 8,198,621 B2 | 6/2012 | Rogers et al. |
| 8,207,473 B2 | 6/2012 | Axisa et al. |
| 8,217,381 B2 | 7/2012 | Rogers |
| 8,431,828 B2 | 4/2013 | Vanfleteren |
| 8,440,546 B2 | 5/2013 | Nuzzo |
| 8,552,299 B2 | 10/2013 | Rogers |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,905,772 B2 | 12/2014 | Rogers |
| 2001/0003043 A1 | 6/2001 | Metspalu et al. |
| 2001/0012918 A1 | 8/2001 | Swanson |
| 2001/0021867 A1 | 9/2001 | Kordis |
| 2002/0021445 A1 | 2/2002 | Boxhevolnyi et al. |
| 2002/0026127 A1 | 2/2002 | Balbierz |
| 2002/0082515 A1 | 6/2002 | Campbell et al. |
| 2002/0094701 A1 | 7/2002 | Biegelsen et al. |
| 2002/0110766 A1 | 8/2002 | Tsai et al. |
| 2002/0113739 A1 | 8/2002 | Howard |
| 2002/0128700 A1 | 9/2002 | Cross, Jr. |
| 2002/0151934 A1 | 10/2002 | Levine |
| 2003/0006527 A1 | 1/2003 | Rabolt et al. |
| 2003/0017848 A1 | 1/2003 | Engstrom et al. |
| 2003/0032892 A1 | 2/2003 | Erlach et al. |
| 2003/0045025 A1 | 3/2003 | Coyle |
| 2003/0082889 A1 | 5/2003 | Maruyama et al. |
| 2003/0087476 A1 | 5/2003 | Oohata et al. |
| 2003/0097165 A1 | 5/2003 | Krulevitch |
| 2003/0138704 A1 | 7/2003 | Mei et al. |
| 2003/0149456 A1 | 8/2003 | Rottenberg et al. |
| 2003/0162507 A1 | 8/2003 | Vatt |
| 2003/0171691 A1 | 9/2003 | Casscells et al. |
| 2003/0178316 A1 | 9/2003 | Jacobs et al. |
| 2003/0214408 A1 | 11/2003 | Grajales |
| 2003/0222282 A1 | 12/2003 | Fjelstad et al. |
| 2003/0227116 A1 | 12/2003 | Halik et al. |
| 2003/0236455 A1 | 12/2003 | Swanson |
| 2004/0005723 A1 | 1/2004 | Empedocles et al. |
| 2004/0006264 A1 | 1/2004 | Mojarradi et al. |
| 2004/0026684 A1 | 2/2004 | Empedocles et al. |
| 2004/0061543 A1 | 4/2004 | Nam et al. |
| 2004/0079464 A1 | 4/2004 | Kumakura |
| 2004/0081384 A1 | 4/2004 | Datesman et al. |
| 2004/0092806 A1 | 5/2004 | Sagon |
| 2004/0095658 A1 | 5/2004 | Buretea et al. |
| 2004/0106334 A1 | 6/2004 | Suzuki |
| 2004/0112964 A1 | 6/2004 | Empedocles et al. |

(56) References Cited

U.S. PATENT DOCUMENTS

| | | |
|---|---|---|
| 2004/0135094 A1 | 7/2004 | Niigaki |
| 2004/0136866 A1 | 7/2004 | Pontis et al. |
| 2004/0138558 A1 | 7/2004 | Dunki-Jacobs |
| 2004/0146560 A1 | 7/2004 | Whiteford et al. |
| 2004/0149921 A1 | 8/2004 | Smyk |
| 2004/0155290 A1 | 8/2004 | Mech et al. |
| 2004/0171969 A1 | 9/2004 | Socci |
| 2004/0178390 A1 | 9/2004 | Whiteford |
| 2004/0178466 A1 | 9/2004 | Merrill |
| 2004/0192062 A1 | 9/2004 | Mikelson |
| 2004/0192082 A1 | 9/2004 | Wagner et al. |
| 2004/0200734 A1 | 10/2004 | Co et al. |
| 2004/0203486 A1 | 10/2004 | Shepherd |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0221370 A1 | 11/2004 | Hannula et al. |
| 2004/0229830 A1 | 11/2004 | Tachibana et al. |
| 2004/0243204 A1 | 12/2004 | Maghribi |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0021103 A1 | 1/2005 | DiLorenzo |
| 2005/0038498 A1 | 2/2005 | Dubrow et al. |
| 2005/0067293 A1 | 3/2005 | Naito |
| 2005/0082526 A1 | 4/2005 | Bedell et al. |
| 2005/0096513 A1 | 5/2005 | Ozguz |
| 2005/0113744 A1 | 5/2005 | Donoghue |
| 2005/0124712 A1 | 6/2005 | Anderson et al. |
| 2005/0133954 A1 | 6/2005 | Homola |
| 2005/0139683 A1 | 6/2005 | Yi |
| 2005/0171524 A1 | 8/2005 | Stern et al. |
| 2005/0177335 A1 | 8/2005 | Crisco |
| 2005/0203366 A1 | 9/2005 | Donoghue |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0003709 A1 | 1/2006 | Wood |
| 2006/0038182 A1 | 2/2006 | Rogers et al. |
| 2006/0049485 A1 | 3/2006 | Pan et al. |
| 2006/0056161 A1 | 3/2006 | Shin et al. |
| 2006/0071349 A1 | 4/2006 | Tokushige |
| 2006/0076561 A1 | 4/2006 | Hicki et al. |
| 2006/0084012 A1 | 4/2006 | Nuzzo et al. |
| 2006/0084394 A1 | 4/2006 | Engstrom et al. |
| 2006/0085976 A1 | 4/2006 | Eldridge et al. |
| 2006/0102525 A1 | 5/2006 | Volkel et al. |
| 2006/0106321 A1 | 5/2006 | Lewinsky et al. |
| 2006/0119853 A1 | 6/2006 | Baumberg et al. |
| 2006/0127817 A1 | 6/2006 | Ramanujan et al. |
| 2006/0128346 A1 | 6/2006 | Yasui |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0154398 A1 | 7/2006 | Qing |
| 2006/0159837 A1 | 7/2006 | Kaplan et al. |
| 2006/0160560 A1 | 7/2006 | Josenhans |
| 2006/0169989 A1 | 8/2006 | Bhattacharya et al. |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0264767 A1 | 11/2006 | Shennib |
| 2006/0273279 A1 | 12/2006 | Kaplan et al. |
| 2006/0279191 A1 | 12/2006 | Geohegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0027514 A1 | 2/2007 | Gerber |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0108389 A1 | 5/2007 | Makela |
| 2007/0123756 A1 | 5/2007 | Kitajima et al. |
| 2007/0187862 A1 | 8/2007 | Kaplan et al. |
| 2007/0212730 A1 | 9/2007 | Vepari et al. |
| 2007/0213616 A1 | 9/2007 | Anderson et al. |
| 2007/0227586 A1 | 10/2007 | Zapalac |
| 2007/0233208 A1 | 10/2007 | Kurtz et al. |
| 2008/0000871 A1 | 1/2008 | Suh et al. |
| 2008/0008626 A1 | 1/2008 | Lin et al. |
| 2008/0038236 A1 | 2/2008 | Gimble et al. |
| 2008/0041617 A1 | 2/2008 | Chen et al. |
| 2008/0046080 A1 | 2/2008 | Bulcke et al. |
| 2008/0054875 A1 | 3/2008 | Saito |
| 2008/0055581 A1 | 3/2008 | Rogers et al. |
| 2008/0074383 A1 | 3/2008 | Dean |
| 2008/0077225 A1 | 3/2008 | Carlin et al. |
| 2008/0085272 A1 | 4/2008 | Kaplan et al. |
| 2008/0090322 A1 | 4/2008 | Mech et al. |
| 2008/0096620 A1 | 4/2008 | Lee |
| 2008/0102096 A1 | 5/2008 | Molin et al. |
| 2008/0108171 A1 | 5/2008 | Rogers et al. |
| 2008/0108942 A1 | 5/2008 | Brister et al. |
| 2008/0139894 A1 | 6/2008 | Szydlo-Moore et al. |
| 2008/0140152 A1 | 6/2008 | Imran |
| 2008/0152281 A1 | 6/2008 | Lundquist et al. |
| 2008/0157234 A1 | 7/2008 | Hong |
| 2008/0157235 A1 | 7/2008 | Rogers et al. |
| 2008/0183076 A1 | 7/2008 | Witte et al. |
| 2008/0188912 A1 | 8/2008 | Stone et al. |
| 2008/0193749 A1 | 8/2008 | Thompson |
| 2008/0203268 A1 | 8/2008 | Hobbs et al. |
| 2008/0203431 A1 | 8/2008 | Garcia et al. |
| 2008/0204021 A1 | 8/2008 | Leussler et al. |
| 2008/0208268 A1 | 8/2008 | Bartic |
| 2008/0211087 A1 | 9/2008 | Mueller-Hipper |
| 2008/0212102 A1 | 9/2008 | Nuzzo et al. |
| 2008/0237840 A1 | 10/2008 | Alcoe |
| 2008/0239755 A1 | 10/2008 | Parker et al. |
| 2008/0257586 A1 | 10/2008 | Chen et al. |
| 2008/0259576 A1 | 10/2008 | Johnson et al. |
| 2008/0280360 A1 | 11/2008 | Kaplan et al. |
| 2008/0287167 A1 | 11/2008 | Caine |
| 2008/0288037 A1 | 11/2008 | Neysmith et al. |
| 2008/0293919 A1 | 11/2008 | Kaplan et al. |
| 2008/0313552 A1 | 12/2008 | Buehler et al. |
| 2009/0000377 A1 | 1/2009 | Shipps et al. |
| 2009/0004737 A1 | 1/2009 | Borenstein et al. |
| 2009/0015560 A1 | 1/2009 | Robinson et al. |
| 2009/0017884 A1 | 1/2009 | Rotschild |
| 2009/0028910 A1 | 1/2009 | DeSimone et al. |
| 2009/0048556 A1 | 2/2009 | Durand |
| 2009/0054742 A1 | 2/2009 | Kaminska et al. |
| 2009/0088750 A1 | 4/2009 | Hushka |
| 2009/0107704 A1 | 4/2009 | Vanfleteren et al. |
| 2009/0149930 A1 | 6/2009 | Schenck |
| 2009/0154736 A1 | 6/2009 | Lee |
| 2009/0184254 A1 | 7/2009 | Miura |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0215385 A1 | 8/2009 | Waters |
| 2009/0221896 A1 | 9/2009 | Rickert et al. |
| 2009/0225751 A1 | 9/2009 | Koenck |
| 2009/0232963 A1 | 9/2009 | Kaplan et al. |
| 2009/0234026 A1 | 9/2009 | Kaplan et al. |
| 2009/0247909 A1 | 10/2009 | Mukumoto |
| 2009/0261828 A1 | 10/2009 | Nordmeyer-Massner |
| 2009/0273909 A1 | 11/2009 | Shin |
| 2009/0289246 A1 | 11/2009 | Schneider et al. |
| 2009/0294803 A1 | 12/2009 | Nuzzo et al. |
| 2009/0317639 A1 | 12/2009 | Axisa et al. |
| 2009/0322480 A1 | 12/2009 | Benedict et al. |
| 2010/0002402 A1 | 1/2010 | Rogers et al. |
| 2010/0028451 A1 | 2/2010 | Kaplan et al. |

(56) References Cited

U.S. PATENT DOCUMENTS

| | | |
|---|---|---|
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0073669 A1 | 3/2010 | Colvin |
| 2010/0090781 A1 | 4/2010 | Yamamoto |
| 2010/0090824 A1 | 4/2010 | Rowell et al. |
| 2010/0096763 A1 | 4/2010 | Kaplan et al. |
| 2010/0117660 A1 | 5/2010 | Douglas |
| 2010/0120116 A1 | 5/2010 | Kaplan et al. |
| 2010/0121420 A1 | 5/2010 | Fiset et al. |
| 2010/0152619 A1 | 6/2010 | Kalpaxis et al. |
| 2010/0176705 A1 | 7/2010 | Van Herpen et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0245011 A1 | 9/2010 | Chatzopoulos et al. |
| 2010/0252840 A1 | 10/2010 | Ibbetson et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0298895 A1 | 11/2010 | Ghaffari et al. |
| 2010/0317132 A1 | 12/2010 | Rogers et al. |
| 2010/0321161 A1 | 12/2010 | Isabell |
| 2010/0324455 A1 | 12/2010 | Rangel et al. |
| 2010/0327387 A1 | 12/2010 | Kasai |
| 2011/0011179 A1 | 1/2011 | Gustafsson |
| 2011/0034912 A1 | 2/2011 | De Graff et al. |
| 2011/0051384 A1 | 3/2011 | Kriechbaum |
| 2011/0054583 A1 | 3/2011 | Litt et al. |
| 2011/0068672 A1 | 3/2011 | Hasnain |
| 2011/0101789 A1 | 5/2011 | Salter et al. |
| 2011/0121822 A1 | 5/2011 | Parsche |
| 2011/0140897 A1 | 6/2011 | Purks et al. |
| 2011/0147715 A1 | 6/2011 | Rogers et al. |
| 2011/0170225 A1 | 7/2011 | Rogers et al. |
| 2011/0171813 A1 | 7/2011 | Rogers et al. |
| 2011/0175735 A1 | 7/2011 | Forster |
| 2011/0184320 A1 | 7/2011 | Shipps |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0266561 A1 | 11/2011 | Rogers et al. |
| 2011/0277813 A1 | 11/2011 | Rogers et al. |
| 2011/0316120 A1 | 12/2011 | Rogers et al. |
| 2012/0016258 A1 | 1/2012 | Webster et al. |
| 2012/0051005 A1 | 3/2012 | Vanfleteren et al. |
| 2012/0052268 A1 | 3/2012 | Axisa et al. |
| 2012/0065937 A1 | 3/2012 | de Graff |
| 2012/0074546 A1 | 3/2012 | Chong |
| 2012/0087216 A1 | 4/2012 | Keung et al. |
| 2012/0091594 A1 | 4/2012 | Landesberger |
| 2012/0092178 A1 | 4/2012 | Callsen |
| 2012/0092222 A1 | 4/2012 | Kato et al. |
| 2012/0105528 A1 | 5/2012 | Alleyne |
| 2012/0108012 A1 | 5/2012 | Yasuda |
| 2012/0157804 A1 | 6/2012 | Rogers et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165759 A1 | 6/2012 | Rogers et al. |
| 2012/0172697 A1 | 7/2012 | Urman |
| 2012/0256308 A1 | 10/2012 | Helin |
| 2012/0261551 A1 | 10/2012 | Rogers |
| 2012/0316455 A1 | 12/2012 | Rahman et al. |
| 2012/0327608 A1 | 12/2012 | Rogers |
| 2013/0041235 A1 | 2/2013 | Rogers et al. |
| 2013/0100618 A1 | 4/2013 | Rogers |
| 2013/0211761 A1 | 8/2013 | Brandsma et al. |
| 2013/0245388 A1 | 9/2013 | Rafferty et al. |
| 2013/0316442 A1 | 11/2013 | Meurville et al. |
| 2013/0320503 A1 | 12/2013 | Nuzzo |
| 2013/0321373 A1 | 12/2013 | Yoshizumi |
| 2014/0140020 A1 | 5/2014 | Rogers |
| 2014/0191236 A1 | 7/2014 | Nuzzo |
| 2014/0216524 A1 | 8/2014 | Rogers |
| 2014/0374872 A1 | 12/2014 | Rogers |
| 2015/0001462 A1 | 1/2015 | Rogers |

FOREIGN PATENT DOCUMENTS

| | | |
|---|---|---|
| JP | 2009-170173 A | 7/2009 |
| WO | WO 99/38211 A1 | 7/1999 |
| WO | WO 03/021679 A2 | 3/2003 |
| WO | WO 2005/122285 A2 | 12/2005 |
| WO | WO 2007/003019 A2 | 1/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/046883 A1 | 4/2010 |
| WO | WO 2010/132552 A1 | 11/2010 |
| WO | WO 2011/003181 A1 | 1/2011 |
| WO | WO 2011/084450 A1 | 7/2011 |
| WO | WO 2013/034987 A3 | 3/2013 |
| WO | WO 2013/170032 A2 | 11/2013 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Canadian Office Action corresponding to co-pending Canadian Patent Application Serial No. CA 2,780,747, Canadian Patent Office, dated Jan. 11, 2016; (7 pages).

European Search Report corresponding to co-pending European Patent Application Serial No. EP 15157473.8, European Patent Office, dated Sep. 15, 2015; (7 pages).

(56) References Cited

OTHER PUBLICATIONS

European Search Report corresponding to co-pending European Patent Application Serial No. EP 15157469.6, European Patent Office, dated Sep. 15, 2015; (6 pages).

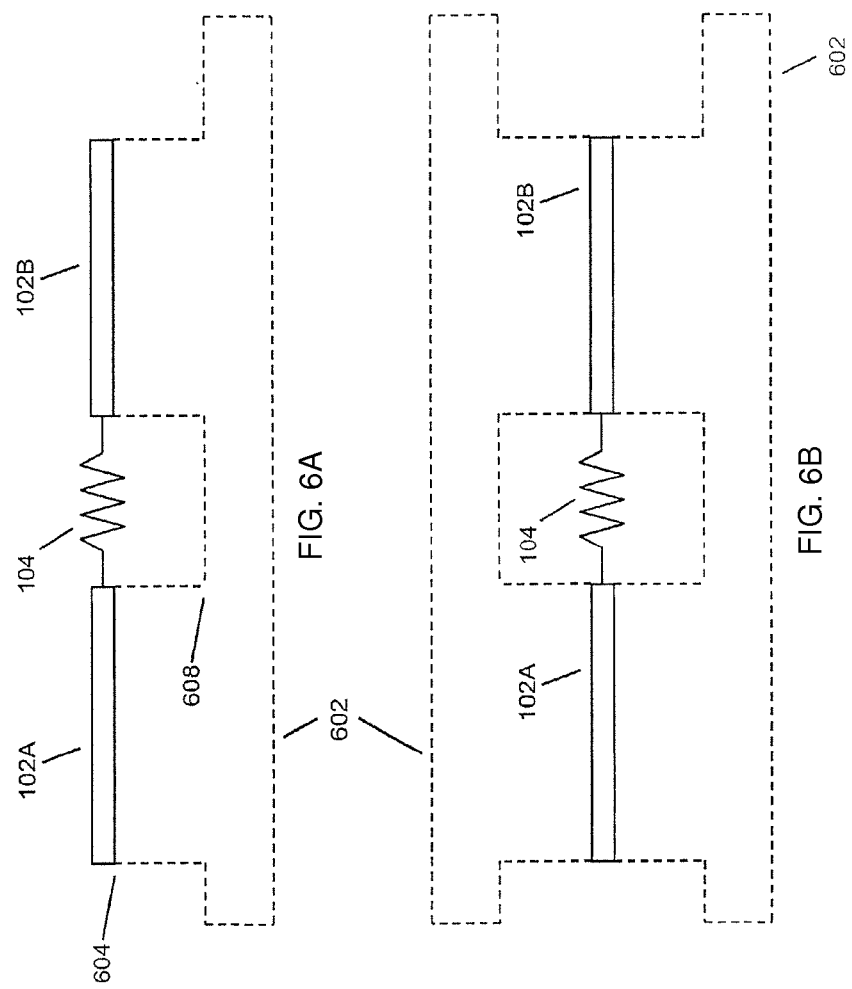

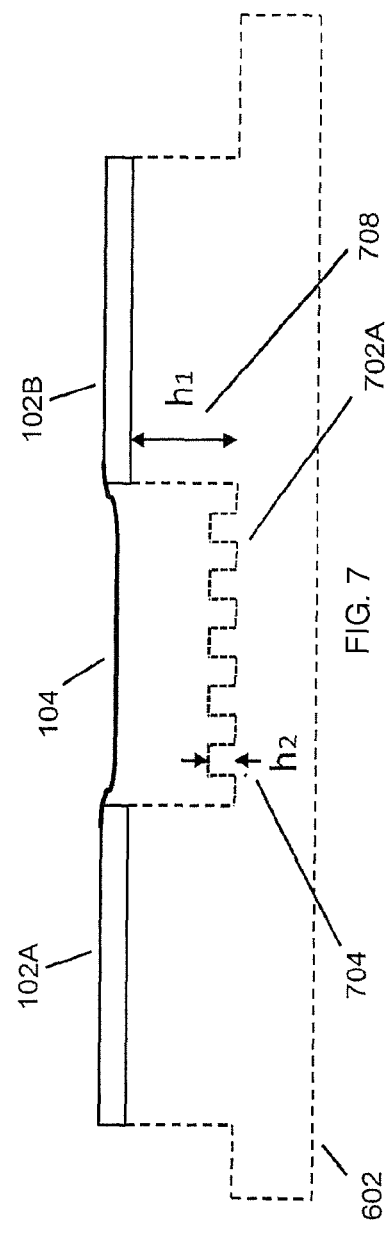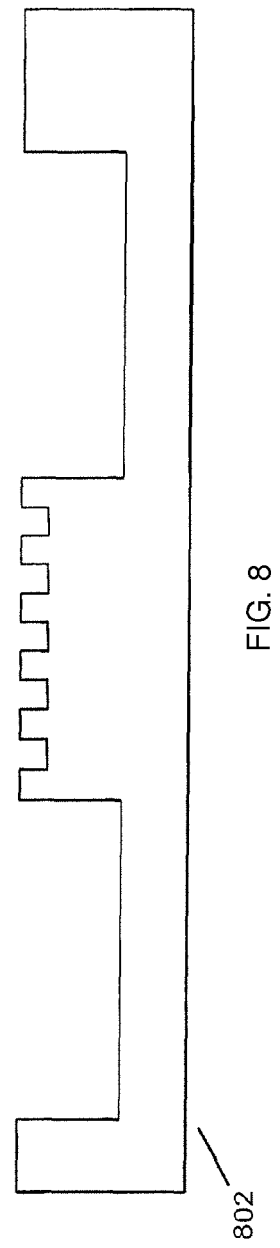

EXTREMELY STRETCHABLE ELECTRONICS

CROSS-REFERENCE TO RELATED APPLICATIONS

This application claims the benefit of U.S. Provisional Application No. 61/113,622 entitled "Extremely Stretchable Interconnects" filed on Nov. 12, 2008, the entirety of which is incorporated herein by reference. Also, this application is a continuation-in-part of, and claims the benefit of U.S. Non-Provisional application Ser. No. 12/575,008, entitled "Catheter Balloon Having Stretchable Integrated Circuitry and Sensor Array" filed on Oct. 7, 2009, the entirety of which is incorporated herein by reference. Application Ser. No. 12/575,008 claimed the priority of U.S. Provisional Application Nos. 61/103,361, filed Oct. 7, 2008 and 61/113,007, filed Nov. 10, 2008 the entirety of each of which is incorporated herein by reference.

FIELD OF THE INVENTION

The present invention relates to systems, apparatuses, and methods utilizing expandable or stretchable integrated circuitry, and more particularly to extremely stretchable integrated circuitry.

BACKGROUND OF THE INVENTION

The field of stretchable electronics continues to grow due to the demand of high performance and mechanically unconstrained applications of the future. However, stretchable electronics have been thus far limited in stretchability. This has limited the ability of stretchable electronics to accommodate applications that require more extreme stretchability. Therefore a need exists for extremely stretchable electronics.

SUMMARY OF THE INVENTION

This invention is for extremely stretchable electrical interconnects and methods of making the same. In embodiments, the invention comprises a method of making stretchable electronics, which in some embodiments can be out of high quality single crystal semiconductor materials or other semiconductor materials, that are typically rigid. For example, single crystal semiconductor materials are brittle and cannot typically withstand strains of greater than about +/−2%. This invention describes a method of electronics that are capable of stretching and compressing while withstanding high translational strains, such as in the range of −100,000% to +100,000%, and/or high rotational strains, such as to an extent greater than 180°, while maintaining electrical performance found in their unstrained state.

In embodiments, the stretching and compressing may be accomplished by fabricating integrated circuits (ICs) out of thin membrane single crystal semiconductors, which are formed into "islands" that are mechanically and electrically connected by "interconnects," and transferring said ICs onto an elastomeric substrate capable of stretching and compressing. The islands are regions of non-stretchable/compressible ICs, while the interconnects are regions of material formed in a way to be highly stretchable/compressible. The underlying elastomeric substrate is much more compliant than the islands, so that minimal strain is transferred into the islands while the majority of the strain is transferred to the interconnects, which only contain electrical connections and not ICs. Each interconnect attaches one island to another island, and is capable of accommodating strain between the two aforementioned islands, including translation, rotation, or a combination of translation with rotation of one island relative to another. Even though the interconnects may be made of a rigid material, they act like weak springs rather than rigid plates or beams. This configuration thereby allows for the making of extremely stretchable electronics.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE DRAWINGS

The invention and the following detailed description of certain embodiments thereof may be understood by reference to the following figures:

FIGS. 6A and 6B depict embodiments of the present invention, where FIG. 6A is a side view of device islands and extremely stretchable interconnects transferred onto an elastomeric substrate. In this case, the substrate has been molded to have posts that are of the same area as the device islands (note that in embodiments these could be smaller or larger than the device islands). The height "h" of the molded post regions may range from, but is not limited to, about 1-1000 μm. The interconnects are located in between these regions as shown, FIG. 6B Side view as before, with a similarly shaped elastomeric superstrate to serve as an encapsulation layer protecting the devices from direct mechanical contact.

FIG. 7 depicts a side view of a two-layer PDMS substrate in an embodiment of the present invention comprising silicon device islands adhered to top layer, free-standing interconnects, and square wave ripples in the lower layer PDMS to promote increased stretching through the substrate.

FIG. 8 depicts an embodiment of the present invention with a side view of two layers of cured jDhotoresist (SU-8 50 and SU-8 2002) used to make the two-layer PDMS substrate described in FIG. 7.

While the invention has been described in connection with certain preferred embodiments, other embodiments would be understood by one of ordinary skill in the art and are encompassed herein.

All documents referenced herein are hereby incorporated by reference.

DETAILED DESCRIPTION OF THE INVENTION

The present invention accomplishes extremely stretchable electronics by forming the electronics on discrete islands 102 of silicon.

With reference to the present invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable", and roots and derivations thereof, when used to modify circuitry or components thereof is also meant to have the meaning ascribed above. Thus, "stretch" and "expand", and all derivations thereof, may be used interchangeably when referring to the present invention.

In embodiments, the discrete islands mention above are discrete operative (in embodiments, arranged in a "device island" arrangement) and are themselves capable of performing the functionality described herein, or portions thereof. In embodiments, such functionality of the operative devices can include integrated circuits, physical sensors (e.g. temperature, pH, light, radiation etc), biological and/or chemical sensors, amplifiers, A/D and D/A converters, optical collectors, electromechanical transducers, piezo-electric actuators, light emitting electronics which include LEDs, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means.

Figure 1:
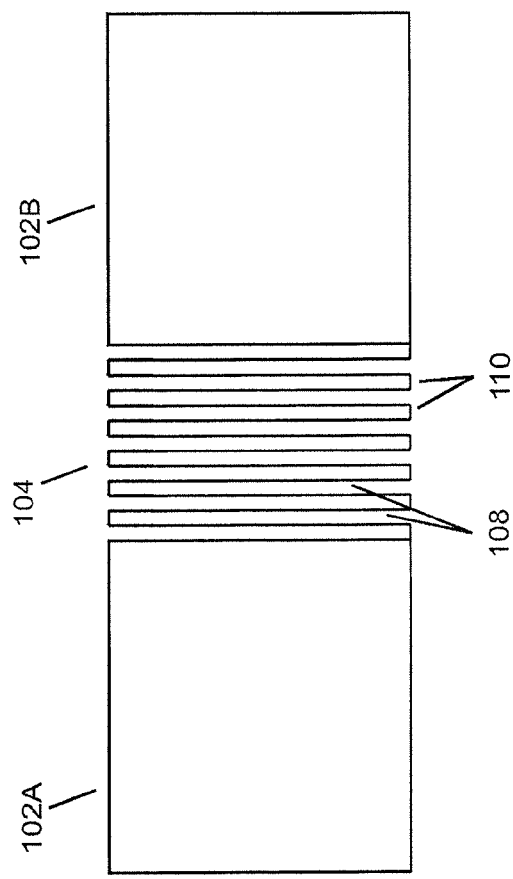
FIG. 1 depicts an overhead view of an embodiment of the present invention showing two device islands connected edge-to-edge by a monolithically formed extremely stretchable interconnect, prior to being stretched.

In an example, the discrete islands 102 may range from about, but not limited to, 10-100 μm in size measured on an edge or by diameter, and connecting said islands 102A-B with one or more extremely stretchable interconnects 104. The novel geometry of the interconnects 104 is what makes them extremely compliant. Each interconnect 104 is patterned and etched so that its structural form has width and thickness dimensions that may be of comparable size (such as their ratio or inverse ratio not exceeding about a factor of 10); and may be preferably equal in size. In embodiments, the dimensions may not be greater than about 5um (e.g. where both dimensions are about 1 μm or less). The interconnect 104 may be formed in a boustrophedonic style such that it effectively comprises long bars 108 and short bars 110 as shown in FIG. 1. This unique geometry minimizes the stresses that are produced in the interconnect 104 when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress.

Figure 2:
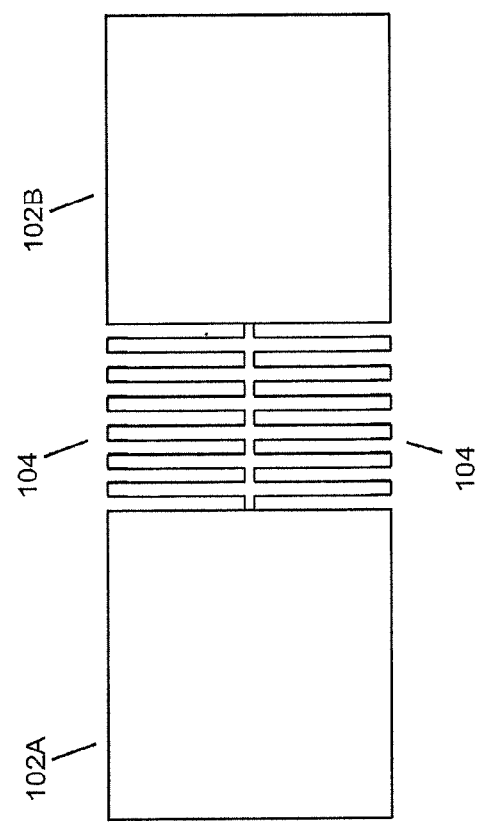
FIG. 2 depicts an overhead view of an embodiment of the present invention showing two device islands connected edge-to-edge by two extremely stretchable interconnects.
Figure 3:
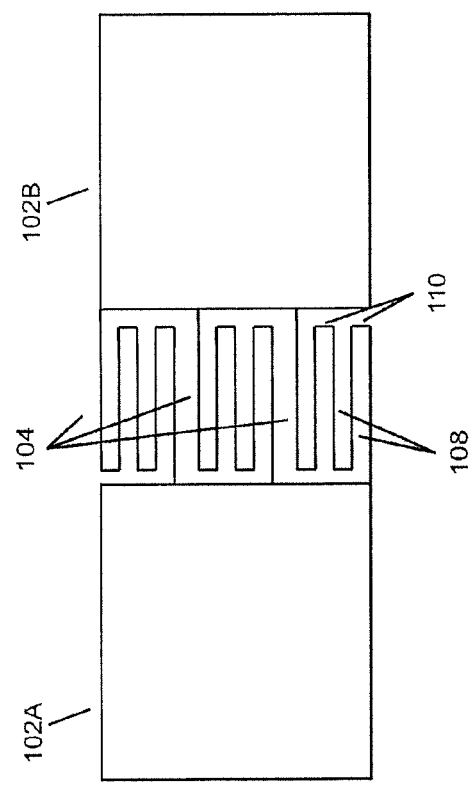
FIG. 3 depicts an overhead view of an embodiment of the present invention showing two device islands connected edge-to-edge by three extremely stretchable interconnects; in this case, the long bars of the interconnects are rotated by 90° which allows them to be longer than if they were not rotated.
Figure 4:
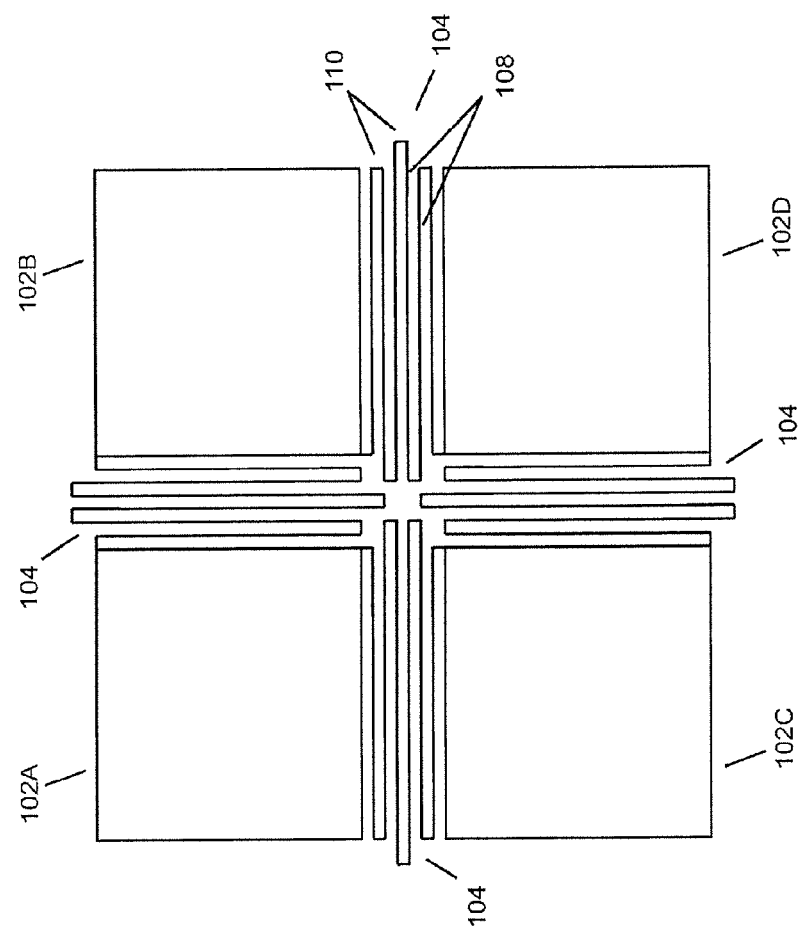
FIG. 4 depicts four device islands arranged in a square matrix in an embodiment of the present invention, with each edge connected by an extremely stretchable interconnect to its nearest neighbors island edge, and the interconnects are formed so as to maximize the amount of chip area that is used for either an island or interconnect.
Figure 5:
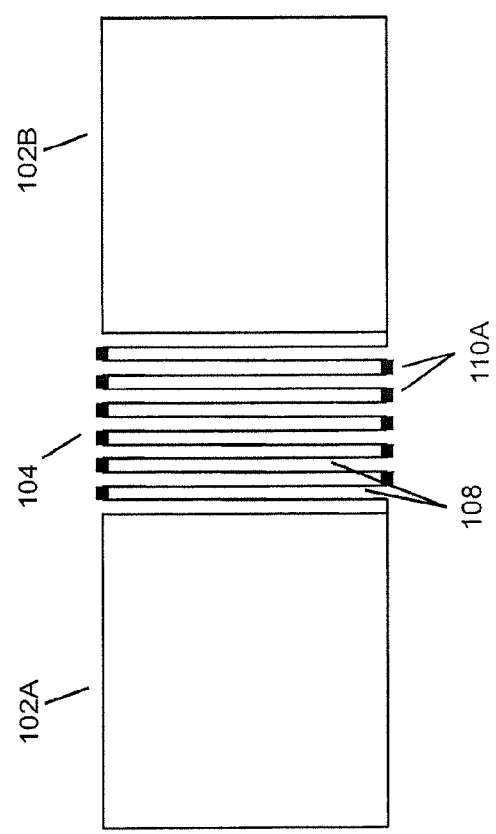
FIG. 5 depicts the case of FIG. 1, with the short bars widened for extra mechanical strength at those locations.

In addition, because the interconnect 104 may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands 102A-B. This is illustrated in FIG. 1. One or more interconnects 104 may be formed in various ways, as shown in FIGS. 2-4. The parts of the interconnect 104 where the majority of stresses build up during stretching may be the short linking bars. To minimize cracking here, the short linking bars 110A may be made several micrometers wider than the longer bars 108, as shown in FIG. 5.

In embodiments, the connection point of the interconnect 104 to the device island 102 may be anywhere along the device island edge, or may be at a point on the surface of the device island 102 (in which case the interconnect may be located just above the plane of the device island).

In embodiments, device islands 102 may be made on any suitable material substrate, provided that a top membrane layer of said substrate that contains the ICs can be freed from the bulk of the substrate and transfer printed onto an elastomeric substrate.

In the present invention, the interconnects 104 (as described herein) may be formed either monolithically (i.e., out of the same semiconductor material as the device islands) or may be formed out of another material. In one non-limiting example embodiment, the stretchable electronics are fabricated on a silicon-on-insulator (SOI) wafer, having a 1 μm thick top silicon layer and a 1 μm thick buried oxide layer. Devices are formed on the top silicon wafer, and arranged into a square pattern of islands 102A-D and interconnects 104 of the general form shown in FIG. 4, in which the islands 102 are 100 μm on an edge, and the interconnects 104 are 1 μm wide, and the space between each long bar is 1 μm, and the interconnects 104 comprise 10 long bars 108, all about 100 jam long. The islands 102 and interconnects 104 are formed in an etching step which removes the excess silicon. The islands 102 and interconnects 104 are coated with a 1 μm layer of polyimide that is patterned to only cover the islands 102 and interconnects 104. Next, the islands 102 and interconnects 104 are released in an HF etch which undercuts the underlying buried oxide. After drying, the islands 102 and interconnects 104 are transfer printed with a Polydimethylsiloxane (PDMS) stamp onto an elastomeric substrate 602. After being picked up by the transfer stamp, and prior to being placed onto the elastomeric substrate 602, the backsides of the islands 102 may be coated with a layer of polyimide (patterned to only cover the islands 102 and interconnects 104), and an additional layer of evaporated 3 nm chromium and 30 nm silicon dioxide selectively over the island regions to improve adhesion to the elastomeric substrate 602 at those locations, and not along the interconnects 102. The elastomeric substrate 602 may be PDMS or another highly compliant material. The elastomeric substrate 602 may additionally be molded or etched into the shape shown in FIG. 6A-B, to further increase selective adhesion in the device island region but not the interconnect region, and to reduce the amount of material strain in the elastomeric substrate 602 that is transferred to the device islands 102. In this example, the interconnects may accommodate stretching the device islands apart by approximately up to 800 µm. In addition, the interconnects 104 of this example may be capable of accommodating lateral shear displacements of about 800 µm. In general, they may be capable of accommodating any relative displacement of the two islands such that they remain approximately within 800 µm of each other. In addition, the interconnects 104 may accommodate corkscrew type rotations of one island relative to another about any of the three axes of rotation. This feature may be limited only by the interconnects becoming entangled within each other. In any practical application, the completed stretchable device may not be so severely rotated, and the interconnect may easily accommodate rotations of up to 180°. It is noted that by increasing the number of long bars 108 used in the interconnect 104, or by increasing the length of the long bars 108, the interconnect may be able to accommodate even larger displacement strains. In embodiments, there may be no practical upper limit to the amount of displacement enabled through the present invention.

In another embodiment the elastomeric substrate 602 may comprise two layers separated by a height. The top "contact" layer contacts the device island 102 as in the embodiment illustrated in FIG. 6. In addition, FIG. 7 shows the bottom layer 702 may be a "wavy" layer containing ripples or square waves molded into the substrate 602 during elastomer fabrication. These square waves enable additional stretching, whose extent depends on the amplitude and wavelength of the waves pattern-molded in the elastomer 602. FIG. 7 shows one non-limiting layout and topology of an elastomeric substrate 602 relative to the position of the interconnects 104 and device islands 102A-B. In an example, a two layer molded substrate can be fabricated using two step process consisting of two types of negative photoresist (SU-8 50 and SU-8 2002; Microchem Corporation). The negative resists can be spin-coated on a transfer silicon wafer with spin speeds of 3000 rpm. The SU-8 50 layer can be spun on the wafer, and subsequently cured with UV radiation. Once the SU-8 50 layer has hardened, the SU-8 2002 can be spun and cured with a photo-mask and an alignment tool. In this example, the thickness of the SU-8 50 and SU-8 2002 are 40-50 µm 708 and 2-10 µm 704, respectively. The 40-50 µm thick regions of SU-8 50 contain ripples 702 of SU-8 2002 (in this instance in the form of square waves) on their surfaces. Upon curing of the SU-8 2002 layer, liquid PDMS can be poured over the SU-8 patterns to form a substrate in the shape of the SU-8 molds 802, as shown in FIG. 8. The amplitude of the ripples in the SU-8 mold 802 can be varied by changing the spin speed used for spinning the thin layer of SU-8 2002. In this configuration, the interconnects 104 are free-standing. The entire substrate-device configuration can be immersed in non-cured elastomer (fluid layer) layer followed by a cured layer of PDMS to encapsulate the fluid and devices.

Figure 9:
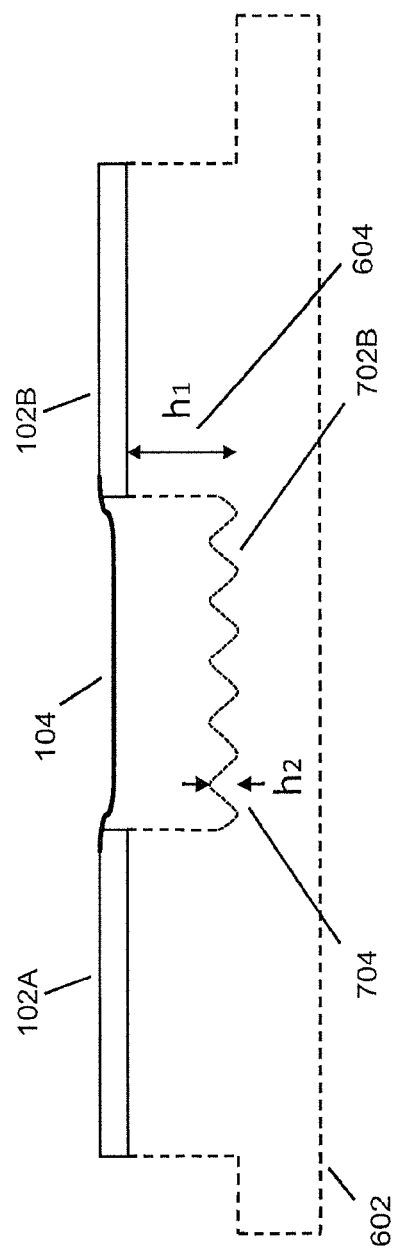
FIG. 9 depicts an embodiment of the present invention with a side view of a two-layer PDMS substrate consisting of sinusoidal waves in the lower layer of PDMS to promote increased stretching through the substrate.

In another embodiment, the PDMS in the lower layer may be designed with periodic sinusoidal ripples 702B. In embodiments, this ripple configuration may be achieved by bonding Si nanoribbons on the surface of pre-strained PDMS in a uniform parallel pattern. The release of the prestrain in the PDMS substrate generates sinusoidal waves along the thin Si-nanoribbons (caused by buckling) and the surface of the PDMS substrate. The amplitude and wavelength of these waves 702B may depend on the extent of uniaxial pre-strain exerted on the PDMS and on the mechanical properties of the Si-nanoribbons. The wavy surface on the PDMS may be used as a transfer mold. Two-part liquid plastic solution can be poured over the wavy PDMS substrate and cured at room temperature over time (~2 hrs). Once the plastic hardens, the plastic substrate can be peeled away from the PDMS. This new plastic transfer substrate with wavy surface features can be used to produce more PDMS substrates containing wave features. The wavy PDMS may serve as the lower layer of PDMS as in the previous embodiment. To produce a two layer PDMS structure, a top layer of PDMS can be plasma bonded to this lower layer of PDMS using oxygen plasma surface activation to produce the substrate illustrated in FIG. 9.

In another embodiment, the PDMS transfer stamp is stretched after the islands 102A-B and interconnects 104 are picked up. A subsequent transfer to another elastomeric substrate 602 may place these pre-stretched devices in a configuration, which allows the new elastomeric substrate to undergo compression. The devices may be able to accommodate that compression because the interconnects are pre-stretched.

In another embodiment, the interconnects 104 are not made out of the same material as the device islands 102. In this case, the islands 102A-B are completely isolated from each other by etching, with no interconnects in between. In an example, a layer of polyimide may then be deposited, contact vias etched to various locations on the surface of the device island 102, and then metal interconnects 104 deposited and patterned into a boustrophedonic pattern, followed by another layer of polyimide. Both layers of polyimide may now be patterned and etched to leave a small border around the interconnects 104 (thereby fully encapsulating the interconnects). These interconnects may have the advantage that they are already fully encapsulated in polyimide and will not adhere as well to the elastomeric substrate as the device islands will. The other advantage is that these interconnects may not be limited to only connecting along the edge of an island. The contact via may be etched anywhere on the surface of the island 102, including near the center. This may allow for easier connections to devices, more connections than possible only along an edge, increased strain compliance, decreased strain at the contact vias, and multiple layers of interconnects made with polymer passivation layers in between, allowing even more interconnects, or allowing one device island 102A to connect to a non-neighboring device island 102B.

In another embodiment of the invention, the device islands 102 are fabricated and transfer printed onto the elastomeric substrate 602, or substrate comprising a polymeric release layer and polymeric non-release layer. After transfer printing, the interconnects 104 are formed as described above, which may be possible because they do not require any high temperature processing, and then in the latter case, the release layer is etched and the devices that are on the non-release layer, are transfer printed onto another elastomeric substrate 602. In the former case, the islands 102 may be transferred onto the elastomeric substrate using pick and place technology so that islands 102 that are initially fabricated very close to each other are spread apart when they are transfer printed. This allows the interconnects 104 to be fabricated in a pattern that resembles their stretched configuration (if desired), to allow compression.

In embodiments, the present invention may comprise a stretchable electrical interconnect 104, including an electrical interconnect 104 for connecting two electrical contacts 102A-B (e.g. device islands 102A-B), where the electrical interconnect 104 may be arranged boustrophedonicially to define rungs 108 (i.e. long bars 108) between the contacts 102A-B, and where the rungs 108 may be substantially parallel with one another and where a plurality of rungs 108 may have substantially the same length and displacement therebetween. In addition, the ratio of the length of the plurality of rungs 108 and the displacement between the plurality of rungs 108 may be large, such as at least 10:1, 100:1, 1000:1, and the like. The electrical integrity of the electrical interconnect 104 may be maintained as stretched, such as to displacements that are increased to 1000%, 10000%, 100000%, and the like during stretching. In embodiments, the rungs 108 may be substantially perpendicular to the contacts 102A-B, the interconnection 104 may have a trace width and/or inter-rung spacing ranging between 0.1-10 microns. In embodiments, the two electrical contacts 102A-B may be located on an elastomeric substrate 602, the electrical contacts 102A-B may be bonded to the substrate 602 and the interconnection 104 not bonded to the substrate 602, the electrical contacts 102A-B may be semiconductor circuits, metal contacts, and the like.

In embodiments, the present invention may comprise a stretchable electrical interconnect 104, including an electrical interconnect 104 for connecting two electrical contacts 102A-B, where the electrical interconnect 104 is arranged boustrophedonicially to define rungs 108 between the contacts 102A-B, and where the interconnect 104 maintains electrical conductivity and electrical integrity when a displacement between the contacts 102A-B is increased, such as by 1000%, 10000%, 100000%, and the like.

In embodiments, the present invention may electrically interconnect two electrical contacts 102A-B with a stretchable interconnection 104 that has the ability to twist between the two electrical contacts 102A-B by up to approximately 180 degrees while maintaining electrical integrity of the stretchable interconnection 104.

In embodiments, the present invention may be a device including a body having a stretchable surface (e.g. an elastomeric substrate 602), and a stretchable electronic circuit including (i) a first discrete operative device 102A, (ii) a second discrete operative device 102B, and (iii) a stretchable interconnect 104 connecting the first discrete operative device 102A to the second discrete operative device 102B, where the interconnect 104 may have a substantially boustrophedonic pattern and be able to maintain electrical conductivity when stretched, such as up to 1000%, 10000%, 100000%, and the like. The stretchable electronic circuit may be affixed to the stretchable surface of the body. In embodiments, the connection may be to a metal contact, to a semiconductor device, and the like. The first discrete operative device 102A, the second discrete operative device 102B, and the stretchable interconnect 104 may all be made from the same material, and that material may be a semiconductor material.

In embodiments, the present invention may attach at least two isolated electronic components (which in embodiments may be discrete operative devices) 102A-B to an elastomeric substrate 602, and arrange an electrical interconnection 104 between the components 102A-B in a boustrophedonic pattern interconnecting the two isolated electronic components 102A-B with the electrical interconnection 104. The elastomeric substrate 602 may then be stretched such that components 102A-B separate relative to one another, where the electrical interconnection 104 maintains substantially identical electrical performance characteristics that the electrical interconnection 104 had in a pre-stretched form. In embodiments, the stretching may be a translational stretching, where the separation between the isolated electronic components 102A-B increases by a percent as a result of the stretching, such as 10%, 100%, 1000%, 10000%, 100000%, and the like. The stretching may be a rotational stretching, where the rotation may be greater than a certain rotation angle, such as 90°, 180°, 270°, 360°, and the like, where the stretching may be in all three axes. In embodiments, the electrical interconnection 104 may be made from semiconductive material. The electrical interconnection 104 may be made from the same semiconductor material as the isolated electronic components 102A-B, fabricated at the same time as the isolated electronic components 102A-B, and the like. The semiconductor material may be a single crystal semiconductor material. The electrical interconnection 104 may made of a different material than the isolated electronic components 102A-B, such as a metal. In embodiments, the interconnect material 104 may be loosely bound to the elastomeric substrate 602, not connected at all, raised above the surface of the elastomeric substrate 602, and the like. In embodiments, the at least two isolated semiconductor circuits may be fabricated on an upper surface 604 of the elastomeric substrate 602 separated by a lower surface 608 of the elastomeric substrate 602, and the electrical interconnection 104 may be fabricated at the level of the upper surface 604 of the elastomeric substrate 602. In this way, the electrical interconnection 104 may have no direct contact with the lower level 608, and thereby be substantially free from adhesion to the lower level 608 during stretching. In addition, the lower surface 608 of the elastomeric substrate 602 may include a wavy form 702, where the wavy form 704 may allow the elastomeric substrate 602 to expand during stretching.

While the invention has been described in connection with certain preferred embodiments, other embodiments would be understood by one of ordinary skill in the art and are encompassed herein.

All documents referenced herein are hereby incorporated by reference.

What is claimed is:

1. A stretchable integrated circuit (IC) system comprising:
a flexible substrate;
a first device island mounted to the flexible substrate and comprising a first integrated circuit (IC) device fabricated from a rigid single-crystal semiconductor;
a second device island mounted to the flexible substrate and comprising a second integrated circuit (IC) device fabricated from a rigid single-crystal semiconductor; and
a flexible electrical interconnect electrically coupling the first IC device to the second IC device, wherein the flexible interconnect includes a polymer passivation layer and maintains electrical connectivity under translational and rotational strains.

2. The stretchable IC system of claim 1, wherein each of the IC devices comprises a thin-membrane single-crystal semiconductor with a width or diameter of about 10-100 micrometers (μm).

3. The stretchable IC system of claim 2, wherein the flexible electrical interconnect electrically and mechanically coupling the first IC device to the second IC device, the flexible electrical interconnect maintains electrical conductivity and integrity under high translational and rotational strains.

4. The stretchable IC system of claim 1, wherein the polymer passivation layer is pattered to only cover the flexible interconnect.

5. The stretchable IC system of claim 1, wherein the polymer passivation layer is patterned to leave a border around the flexible interconnect.

6. The stretchable IC system of claim 1, wherein the polymer passivation layer includes polyimide.

7. The stretchable IC system of claim 6, wherein the polyimide polymer passivation layer covers at least a portion of the first device island and the second device island.

8. The stretchable IC system of claim 1, wherein the first and second IC devices each comprises one or more physical sensors, one or more chemical sensors, one or more packaged light emitting diodes (LED), or any combination thereof.

9. The stretchable IC system of claim 8, wherein the first IC device comprises at least one of the physical sensors, the at least one physical sensor selected from a group consisting of: temperature sensors, pH sensors, light sensors, and radiation sensors.

10. The stretchable IC system of claim 1, wherein the first IC device comprises a high performance microprocessor and the second IC device comprises a physical sensor, a chemical sensor, an LED, or any combination thereof.

11. The stretchable IC system of claim 1, wherein the first and second IC devices each comprises at least one high performance biological sensor, the at least one high performance biological sensor selected from a group consisting of: electrophysiological sensors, skin temperature sensors, and skin pH sensors.

12. The stretchable IC system of claim 1, wherein the first and second device islands include a thin polymeric layer between each device island and the flexible elastomeric substrate.

13. The stretchable IC system of claim 1, wherein the first and second device islands and the flexible electrical interconnect are encased within the flexible elastomeric substrate.

14. The stretchable IC system of claim 1, wherein the first and second device islands are adhered to the flexible elastomeric substrate, and wherein the flexible electrical interconnect lacks adhesion to the elastomeric substrate.

15. The stretchable IC system of claim 1, wherein the flexible electrical interconnect includes rectilinear rungs connected by rectilinear short bars.

16. The stretchable IC system of claim 15, wherein a plurality of the rungs are parallel or substantially parallel with one another, and a plurality of the short bars are parallel or substantially parallel with one another.

17. The stretchable IC system of claim 16, wherein the plurality of the rungs have substantially the same length and have substantially the same displacement therebetween.

18. The stretchable IC system of claim 15, wherein a ratio of the length of the plurality of the rungs and the displacement between the plurality of the rungs is at least about 10:1.

19. The stretchable IC system of claim 18, wherein each of the rungs has a respective width of about 0.1-10 microns.

20. The stretchable IC system of claim 1, wherein the flexible electrical interconnect includes two interconnect layers separated by a polymer passivation layer.

21. The stretchable IC system of claim 1, wherein the flexible electrical interconnect is configured to maintain electrical integrity and conductivity when a distance between the first and second IC devices is increased by 1000%.

22. The stretchable IC system of claim 1, wherein the flexible electrical interconnect is configured to maintain electrical integrity and conductivity when the first and second IC devices are twisted up to approximately 180 degrees.

23. The stretchable IC system of claim 1, wherein the flexible electrical interconnect includes a metal material.

24. The stretchable IC system of claim 1, wherein the flexible electrical interconnect includes a semiconductor material.

25. The stretchable IC system of claim 24, wherein the semiconductor material of the flexible electrical interconnect is the same or substantially the same as the single-crystal semiconductor material.

26. A method of making a stretchable integrated circuit (IC) system, the method comprising:
    mounting a first device island comprising a first integrated circuit (IC) device fabricated from a rigid single-crystal semiconductor to a polymer layer;
    mounting a second device island comprising a second integrated circuit (IC) device fabricated from a rigid single-crystal semiconductor to the polymer layer;
    electrically connecting the first device island to the second device island by a flexible electrical interconnect formed on the polymer layer; and
    adhering the first device island and the second device island to a flexible elastomeric substrate.

27. The method according to claim 26, wherein the polymer layer includes polyimide.

28. The method according to claim 26, wherein the polymer layer is patterned to only cover the device islands and flexible electrical interconnect.

29. The method according to claim 28, wherein the polymer layer is patterned to leave a border around the flexible electrical interconnect.

30. The method according to claim 26, wherein the flexible electrical interconnect is encapsulated in the polymer layer.

31. The method according to claim 26, wherein the first device island, the second device island and the flexible electrical interconnect are encapsulated in the flexible elastomeric substrate.

32. The method according to claim 26, wherein the flexible electrical interconnect includes a metal material.

33. The method according to claim 26, wherein the flexible electrical interconnect includes a semiconductor material.

* * * * *